(12) United States Patent
Rutanen

(10) Patent No.: US 7,892,774 B2
(45) Date of Patent: Feb. 22, 2011

(54) DIAGNOSTIC METHOD FOR DETERMINING THE SUSCEPTIBILITY TO DELIVERY AND REAGENT KIT FOR USE THEREFOR

(75) Inventor: Eeva-Marja Rutanen, Espoo (FI)

(73) Assignee: Oy Medix Biochemica AB, Kauniainen (FI)

( * ) Notice: Subject to any disclaimer, the term of this patent is extended or adjusted under 35 U.S.C. 154(b) by 0 days.

(21) Appl. No.: 12/649,156

(22) Filed: Dec. 29, 2009

(65) Prior Publication Data

US 2010/0099117 A1    Apr. 22, 2010

Related U.S. Application Data

(63) Continuation of application No. 12/498,830, filed on Jul. 7, 2009, which is a continuation of application No. 11/048,685, filed on Jan. 31, 2005, which is a continuation of application No. 08/360,815, filed as application No. PCT/FI1993/00275 on Jun. 29, 1993.

(30) Foreign Application Priority Data

Jun. 29, 1992   (FI) ...................................... 923025

(51) Int. Cl.
    G01N 33/53    (2006.01)
(52) U.S. Cl. ...................... 435/7.92; 435/7.1; 435/7.94; 435/975; 436/501; 436/510; 436/514; 436/524; 436/528; 436/65; 436/814; 600/33
(58) Field of Classification Search ............... 435/7.92, 435/7.94, 975, 7.1; 436/501, 510, 524, 528, 436/548, 65, 87, 814, 514; 600/33
See application file for complete search history.

(56) References Cited

U.S. PATENT DOCUMENTS

| 4,952,517 A | 8/1990 | Bahar |
| 5,037,735 A | 8/1991 | Khanna et al. |
| 5,096,830 A | 3/1992 | Senyei et al. |
| 5,252,459 A | 10/1993 | Tarcha et al. |
| 5,554,504 A | 9/1996 | Rutanen |
| 5,597,700 A | 1/1997 | Konstantinov et al. |

FOREIGN PATENT DOCUMENTS

| EP | 0316919 A2 | 5/1989 |
| WO | WO-89/09268 A1 | 10/1989 |
| WO | WO-90/00569 A1 | 1/1990 |
| WO | WO-92/12426 A1 | 7/1992 |
| WO | WO-9958974 A1 | 11/1999 |

OTHER PUBLICATIONS

Rutenen et al., Biochem. and Biophys. Res. Comm., vol. 152, No. 1, pp. 208-215 (Apr. 15, 1988).
Rutanen et al., Endocrinology, vol. 116, No. 4, pp. 1304-1309 (1985).
Pekonen et al., Journal of Immunoassay, 10(4), pp. 325-337 (1989).
Koistinen et al., Endocrinology, vol. 118, No. 4, pp. 1375-1378 (1986).
Rutanen et al., Am. J. Obstet. Gynecol., vol. 144, No. 4, pp. 460-463 (Oct. 15, 1982).
Koistinen et al., Clin. Chim. Acta., 164(3), pp. 293-303, (May 15, 1987) Absract Only.
Bishop, Obstetrics and Gynecology, vol. 24, No. 2, pp. 266-268 (Aug. 1964).
Lockwood et al., "Fetal membrane rupture is associated with the presence of insulin-like . . . ", vol. 171, (Jul. 1994), pp. 146-150. Am. J. Obstet. Gynecol.
Westwood et al., "The phosphorylation patter of insulin-like growth factor-binding protein-1 . . . ", Journal of Clinical Endocrinology and Metabolism, vol. 79, No. 6, Dec. 1994, pp. 1735-1741.
Bohn et al., Arch. Gynecol., 229, pp. 279-291 (1980).
Rutanen et al., British Journal of Obstetrics and Gynecology, 279-291 (1980).
Rutanen et al., British Journal of Obstetrics and Gynecology, vol. 91, pp. 1240-1244 (Dec. 1984).
Alister Voller, Enzyme-Immunoassay, Chapter 9, pp. 181-196 (1980).
Friedman et al., Am. J. Obst. & Gynec., vol. 104, No. 4, pp. 544-550.
Povoa et al., Endocrinology, 107:563-570 (1984).
Lee et al., Molecular Endocrinology, vol. 2, No. 5, pp. 404-411 (1988).
Koninckx et al., British Journal of Obstetrics and Gynecology, vol. 88, pp. 607-610 (Jun. 1981).

(Continued)

Primary Examiner—Shafiqul Haq
Assistant Examiner—James L Grun
(74) Attorney, Agent, or Firm—Birch, Stewart, Kolasch & Birch, LLP

(57) ABSTRACT

The invention relates to a diagnostic method for detecting susceptibility to delivery, and to a test kit for this purpose. A low, but higher than baseline level concentration of Insulin-like Growth Factor Binding Protein 1 (IGFBP-1), which is due to leakage from decidual cells, is detected by an immunological assay in a vaginal secretion sample.

9 Claims, No Drawings

OTHER PUBLICATIONS

Rochelson et al., Obstetrics & Gynecology, vol. 62, No. 4, pp. 414-418 (Oct. 1983).

Rutanen et al., Am. J. Obstet. Gynecol., vol. 164, No. 1, p. 258, Abstract 38 (Jan. 1991).

Rutanen et al., Clinica Chimica Acta, vol. 214, pp. 73-81 (1993).

Rutanen et al., Clinica Chimica Acta, vol. 253, pp. 91-101 (1996).

Lockwood et al., New Eng. J. Med., vol. 325, pp. 669-674 (1991).

Koistinen et al., Clinica Chimica Acta, vol. 215, pp. 189-199 (1993).

Khosravi et al., "Immunoassay of insulin-like growth factor binding protein-1", Clin. Chem., 1997, vol. 43, pp. 523-532.

Nuutila et al., "Phosphorylated isoforms of insulin-like growth factors binding protein-1 in the cervix as a predictor of cervical ripeness", Obstetrics & Gynecology, 1999, vol. 94, pp. 243-249.

Andersen et al., "Preterm labor", in Danforth's Obstetrics and Gynecology, 6th Edition, (Scott et al., eds.) J.B. Lippincott, Philadelphia, 1990, pp. 335-351.

Decision on Appeal from U.S Appl. No. 11/048,685, dated Aug. 6, 2009.

DIAGNOSTIC METHOD FOR DETERMINING THE SUSCEPTIBILITY TO DELIVERY AND REAGENT KIT FOR USE THEREFOR

This application is a Continuation of co-pending U.S. application Ser. No. 12/498,830 filed on Jul. 7, 2009, which is a Continuation of co-pending U.S. application Ser. No. 11/048,685 filed on Jan. 31, 2005, which is a Continuation of co-pending application Ser. No. 08/360,815 filed on Dec. 29, 1994 and for which priority is claimed under 35 U.S.C. §120. Application Ser. No. 08/360,815 is the national phase of PCT International Application No. PCT/FI93/00275 filed on Jun. 29, 1993 under 35 U.S.C. §371. The entire contents of each of the above-identified applications are hereby incorporated by reference. This application also claims priority of Application No. 923025 filed in FINLAND on Jun. 29, 1992 under 35 U.S.C. §119.

The present invention relates to a diagnostic method for determining susceptibility to delivery based on a determination of a protein in a secretion sample taken from the vagina or the uterine cervix of a pregnant woman, and to a test kit designed for this purpose. Determination of susceptibility to delivery is particularly important in terms of the appropriate timing of induction of delivery when the pregnancy is post-term, or when a risk of preterm delivery is suspected.

Post-term pregnancies are a common yet difficult problem in connection with delivery. A pregnancy exceeding 41-42 weeks is considered post-term. Post-term pregnancies account for about 7-12% of all pregnancies, the duration of the pregnancy being calculated from the first day of the last menstrual period. About 4% of all pregnancies continue over 43 weeks. Diagnosis is difficult, even when the first day of the last menstrual period is known. Post-term pregnancy is associated with increased foetal and neonatal morbidity and mortality.

Perinatal mortality increases after the 42nd week of gestation, and doubles after the 43rd week.

Monitoring the well-being of the foetus is vital in cases of post-term pregnancy; delivery is, of course, immediately induced if there are any signs of foetal distress. If, on the other hand, the foetus is well, the next step is to decide the appropriate time for induction. It is generally accepted that labour should be induced as soon as the cervix is "mature" (shorter, softer and possibly partly dilated). Attempts to induce labour too early, i.e. when the cervix is not mature, lead to an increase in the number of sections. On the other hand, if the status of the foetus requires rapid delivery and it is known for sure that the cervix is not mature, the decision will be to operate right away.

The maturity of the cervix is usually determined using the so-called Bishop's score (Bishop E H, *Obstet. Gynecol.* 1964; 24: 266). The Bishop method involves assessing, by palpation, the size of the cervical orifice and the length, softness and direction of the cervical canal. The prior art method for determining the maturity of the cervix is not always sufficient for reliably predicting the time of delivery or for the timing of the induction of labour and estimating the likelihood of success.

Attempts to induce dilation of the cervix are not always successful. Prolonged labour increases the risk of maternal and foetal infection and the risk of foetal asphyxia, as well as being a psychologically unpleasant experience for the mother. Methods for more accurate assessment of the maturity of the cervix are therefore needed.

The present invention uses a completely new approach for predicting the time of delivery. The maturity of the cervix is assessed by determining the level of IGFBP-1, Insulin-like Growth Factor Binding Protein 1, produced by decidual cells, said assessment being performed on a vaginal or cervical secretion sample taken from a pregnant woman.

As the cervix matures and painless uterine contractions increase, the decidua, i.e. the endometrial lining of the mother's uterus and the chorion attached thereto start to become detached from each other in the lower segment of the uterus. When this happens, decidual cells become damaged and compounds synthesized by said cells are likely to "leak" from the cervix into the vagina.

The inventor of the present invention realized that a low but higher than a normal baseline IGFBP-1 concentration in a vaginal or cervical secretion is indicative of such "leakage" and is related to the maturation of the cervix and thus indicates an impending delivery. If no such maturation takes place in the lower segment of the uterus, the chorion remains attached to the decidua and no decidual cell product is found in said secretion.

Determination of IGFBP-1 can therefore function as a biochemical test for assessing the maturity of the cervix and thus the time of delivery, or for deciding when induction should be started. Said test can also be used to identify women in whom induction probably would not help to dilate the cervix, thus helping to prevent prolonged induction attempts, with the attendant risks to both foetus and mother.

Another situation where a correct estimate of the time of delivery is critical, is when a preterm delivery is suspected. Predicting a preterm delivery is difficult. Identification of the risk factors involved helps to predict only a very small proportion of preterm deliveries.

Predicting a preterm delivery on the basis of uterine contractions is often difficult. Preterm contractions may be so weak that neither the woman nor the attendant nurse or physician will notice them. On the other hand, out of the women who feel preterm contractions and whose contractions are also objectively verifiable, only about 10-20% are believed to need treatment to prevent a possibly impending preterm delivery. It is difficult to identify these 10-20%. However, in order to minimize the number of preterm deliveries, it would be important to be able to identify such patients as early as possible, i.e. as soon as contractions start appearing.

Patients having any of the risk factors indicative of preterm labour should be especially closely monitored. In ideal cases, after a positive result in a test predicting preterm labour, a preterm delivery could be better prevented by medication and changes in lifestyle. Diagnosed preterm rupture of foetal membranes and vaginal bleeding are as such signs of impending preterm labour, and laboratory tests are not needed in such cases. However, if the foetal membranes are intact, only regular contractions and observed changes in the cervical canal (shortening of the canal and opening of the orifice to 2 cm or more) are generally considered diagnostic criteria for an impending preterm delivery and indications for hospital admission. This may, in certain cases, prove to be too late.

Several scoring systems have been developed for predicting the risk of preterm labour. The scores are calculated during the first pregnancy examination and used later for purposes of comparison. However, these prior art systems only help to chart about half of the pregnancies that end in preterm delivery. On the other hand, based on said scoring systems, many women who do not deliver their babies preterm end up in the risk group. Attempts have been made to devise biochemical tests (e.g. determination of blood oestradiol, blood progesterone and prostaglandin levels) but with poor results.

The methods used so far have not provided a reliable basis for predicting the significance of preterm contractions and thus the likelihood of preterm labour. Therefore, it has not been possible to direct prophylactic treatment at the right group of pregnant women. In some women, preterm contractions are so weak that they remain unnoticed until the labour is so advanced and the cervix so dilated that the foetal membranes rupture. The only choice is to treat those women who already have clinically observable contractions. However, only in certain cases do preterm contractions lead to preterm labour, and thus only this portion of the women who have clinically confirmed preterm contractions need prophylactic treatment (rest and tocolytic agents, i.e. agents inhibiting uterine contractions). On the other hand, it has been found that tocolytic treatment is ineffective and that preterm labour cannot be prevented if considerable changes have already taken place in the cervix before the medication is started.

The method according to the present invention, wherein the amount of IGFBP-1 in a vaginal or cervical secretion sample is determined, can be used in the prediction of preterm labour.

The protein IGFBP-1 is a product of the decidual cells. It is found in the vaginal secretion of non-pregnant women only during menstruation. Urine and seminal plasma, which may be present in the vagina of pregnant women, contain only very low concentrations of IGFBP-1.

The inventor of the present invention, Eeva-Marja Rutanen, has previously shown that rupture of the foetal membranes can be confirmed by determining the IGFBP-1 concentration in a vaginal secretion. International Patent Application PCT/FI91/00413 is based on said observation. It was also shown that vaginal secretion may contain small amounts of IGFBP-1 even if the foetal membranes are intact.

It can generally be assumed that biological membranes such as foetal membranes may allow the passage of small amounts of compounds and leak fluids such as amniotic fluid into the vagina even if the membranes are intact. This would result in steady or occasional low concentrations of IGFBP-1 in the vaginal or cervical secretion. The inventor of the present invention realized that a rising but low IGFBP-1 level does not represent the baseline level that would result from amniotic fluid leaking through intact membranes. The IGFBP-1 present in the secretion is not a result of ruptured membranes either, since its level is low; instead it originates from decidual cells in which some change is taking place. This change is the detachment of foetal membranes from each other which occurs before labour.

Low IGFBP-1 concentrations probably result from leakage from decidual cells in the lower segment of the uterus, which may happen when the decidual membrane and the chorion become detached from each other as uterine contractions increase. A high IGFBP-1 concentration in the secretion therefore indicates the presence of amniotic fluid, i.e. rupture of the membranes, whereas low concentrations indicate protein secretion from the decidual cells into the cervical canal and changes in the chorion-decidual border, which in turn reflects subclinical changes in the cervix.

The use of a protein (foetal fibronectin) produced by chorionic cells to indicate the rupture of foetal membranes is described in European Patent Application EP 316919. Said Application discloses that high fibronectin levels indicate a rupture of the membranes, thus indicating impending preterm labour (see also Lockwood C J, Senyei A E, Dische M R et al., *New Engl. J. Med.* 1991; 325: 669). However, the disclosed method has the disadvantage that the concentration of foetal fibronectin is high in seminal plasma, which represents a major source of error. Another factor that lowers the value of said method is that the ratio between foetal fibronectin concentrations in serum and in amniotic fluid is not as good as it is for IGFBP-1. This means that there is a greater risk that an unnoticed small blood contamination could interfere with the determination. A test was performed wherein protein levels were determined from vaginal secretion in 20 women whose foetal membranes were intact and who did not have uterine contractions. The fibronectin test gave four positive results, whereas IGFBP-1 determination gave no positive results.

The above European Patent Application does not suggest the use of low fibronectin values for determining susceptibility to delivery when foetal membranes are intact.

In situations where a test is used to predict the time of delivery, it is valuable to obtain the test result rapidly. The ideal test for this purpose would be simple and quick to perform, preferably as a bed-side test, i.e. immediately on the site.

An object of the present invention is to provide a new and improved method for determining the maturity of the cervix and the risk of impending preterm labour, the method being specific to the substance to be measured independent of individual patient variations.

It is also an object of the present invention to provide a method for determining the susceptibility to delivery, the method being rapid and simple to perform, preferably while the patient is waiting (bed-side test).

Another object of the invention is to develop a test kit suitable for such a diagnosis, the kit containing the means for performing a simple and rapid diagnostic test.

The details of the present invention will be evident from the following description and the appended claims, the contents of which are included herein by this reference. Thus, the present invention concerns a diagnostic method for determining susceptibility to delivery, said method being based on the determination of a protein in a vaginal or cervical secretion sample of a pregnant woman. According to the invention, leakage of IGFBP-1 from decidual cells is determined by detecting, in an essentially blood-free secretion sample, that the IGFBP-1 concentration has increased to a level which is higher than the normal baseline level during pregnancy, but still lower than the high IGFBP-1 level caused by the presence of amniotic fluid due to a rupture of the foetal membranes. The presence of IGFBP-1 in the sample is best shown using an IGFBP-1-specific binding substance or substances, preferably an IGFBP-1 monoclonal antibody.

The test kit for the diagnosis of susceptibility to delivery according to the present invention includes at least one reagent in which there is an IGFBP-1 specific binding substance for showing an elevated but still low IGFBP-1 level in a vaginal or cervical secretion sample. The test kit according to the invention also includes at least one label for indicating the binding reaction between IGFBP-1 and said binding substance. The signal(s) indicating the reagent binding reaction is/are chosen so that when the IGFBP-1 concentration of said sample exceeds the normal baseline level during pregnancy, a positive signal is obtained to indicate the binding reaction, and when the IGFBP-1 concentration exceeds the high IGFBP-1 level caused by amniotic fluid, another positive signal is obtained.

The preferred specific binding substance for IGFBP-1 is a specific antibody of IGFBP-1, particularly a monoclonal antibody.

The protein IGFBP-1 was first isolated from the placenta and foetal membranes in 1980 (Bohn et al., *Arch. Gynecol.* 1980; 229: 279-291). It was considered to be a protein of placental origin, it was given the name Placental Protein 12 (PP12). Later, it was observed that PP12 and IGFBP-1 isolated from amniotic fluid had the same N-terminal amino acid sequence and that PP12 binds IGF I (insulin-like growth factor I) (Koistinen et al., *Endocrinology* 1986; 118: 1375).

Synthesis of IGFBP-1 in the decidua of a pregnant woman was first demonstrated in 1985 (Rutanen et al., *Endocrinology* 1985; 116: 1304).

The concentration of IGFBP-1 in amniotic fluid has been found to be usually 100 to 1000 times higher than that in maternal serum (Rutanen et al., *Am. J. Obstet. Gynecol.* 1982; 144:460). The clinical application of this finding is the basis for Patent Application PCT/FI91/00413 (priority date Dec. 30, 1990) assigned to the same applicant. According to said invention a suitably unsensitized test is used for detecting the presence of IGFBP-1 in the vagina caused by a rupture of the foetal membranes. Detecting the rupture of the foetal membranes using IGFBP-1 is also described in an article (Rutanen E-M, Pekonen F., *Am. J. Obstet. Gynecol.* 1991; 164 (Suppl): 258).

The presence of IGFBP-1 after rupture of the foetal membranes is basically a single event involving a sharp, clear elevation, whereas decidual leakage of IGFBP-1 and its presence in the secretion are characterized by gradual elevation as the time of delivery approaches, i.e. as the cervix matures, an event that never leads to very high concentrations.

The reactions based on specific binding substances are widely known. Antibodies are the compounds most commonly used as specific binding substances. These so-called immunological assays are based on the ability of an antibody to bind specifically to a certain site in its antigen (epitope). Polyclonal antibodies are a mixture of immunoglobulins present in the serum of an immunized animal. The mixtures vary between individual animals. Monoclonal antibodies, on the other hand, are produced by one cell line cultured in a laboratory. Such antibodies are homogeneous and can be characterized by methods used in protein chemistry; they can be produced continuously in identical form.

An immunological assay can involve the use of only one antibody. In this case, the reaction conditions are usually chosen so as to allow the antigen in the test sample to compete with an added labelled antigen for a limited number of binding sites in the antibody. Except for said label, said added antigen is identical with the test sample antigen. The concentration of the sample antigen is obtained by determining the fraction of bound label. Several labelling substances that produce a signal enabling measurement of concentration may be used, e.g., radioactive isotopes, enzymes, and chemiluminescent or fluorescent compounds. The method may also employ two different antibodies (the so-called sandwich principle). Here, the antibodies are specific to separate epitopes in the same antigen, and can bind simultaneously to the same antigen molecule. One antibody is usually immobilized on a solid carrier and the other one is labelled. Both antibodies bind to the antigen in the sample, and the complex can be separated from unbound label with the aid of said carrier. The amount of bound labelled antibody is directly proportional to the antigen concentration in the sample.

The present inventor has studied placental proteins, and for her own research work she has developed a radioimmunological assay method for detecting IGFBP-1 (PP12). Monoclonal anti-bodies to IGFBP-1 have also been developed for research purposes (Rutanen et al., *Biochem. Biophys. Res. Commun.* 1988; 152: 208 and Pekonen et al., *J. Immunoassay.* 1989; 10: 325-337).

No report has been found in the literature showing a comparison between the concentrations of IGFBP-1 in amniotic fluid and in other secretions present in the vagina. A research group led by the present inventor has studied the concentrations of IGFBP-1 in amniotic fluid and blood (Table 1), as well as the concentrations in secretions that can be present in the vagina.

TABLE 1

Concentrations of IGFBP-1 in maternal serum (S) and amniotic fluid (AF) in samples taken at gestation of 24-38 weeks.

| Patient | IGFBP-1 S (µg/l) | IGFBP-1 AF (µg/l) | IGFBP-1 ratio AF/S |
|---|---|---|---|
| 1 | 170 | 60000 | 353 |
| 2 | 130 | 29000 | 223 |
| 3 | 140 | 48000 | 343 |
| 4 | 200 | 65000 | 325 |
| 5 | 63 | 22000 | 349 |
| 6 | 350 | 350000 | 1000 |
| 7 | 240 | 115000 | 479 |
| 8 | 190 | 40000 | 210 |
| 9 | 240 | 50000 | 208 |
| 10 | 250 | 200000 | 800 |
| 11 | 130 | 70000 | 538 |
| 12 | 65 | 33000 | 508 |
| 13 | 600 | 70000 | 117 |
| 14 | 260 | 95000 | 365 |
| 15 | 340 | 180000 | 529 |
| 16 | 500 | 155000 | 310 |
| 17 | 155 | 19000 | 122 |
| 18 | 340 | 140000 | 412 |
| 19 | 160 | 200000 | 1250 |
| 20 | 240 | 160000 | 667 |
| 21 | 340 | 145000 | 426 |
| 22 | 350 | 53000 | 151 |
| 23 | 200 | 125000 | 625 |
| 24 | 135 | 55000 | 407 |
| 25 | 340 | 145000 | 426 |

In the paired blood and amniotic fluid samples studied, the concentration of IGFBP-1 in the amniotic fluid was in all cases more than 100 times higher than in maternal serum.

It has also been shown that vaginal secretions as such, sperm and urine contain almost no IGFBP-1. The test according to the present invention can thus be designed so that the presence in the sample of such secretions does not cause false positive results in test situations.

According to the inventor's observations, the concentration of IGFBP-1 in vaginal or cervical secretions can be elevated even when the foetal membranes are intact. However, in a sample extracted in 0.5 ml of a buffer, the IGFBP-1 concentration does not exceed about 100 µg/l, unless it originates from amniotic fluid resulting from ruptured foetal membranes. This finding has brought to light the fact that, when the foetal membranes remain intact, this slight but higher than baseline elevation can be interpreted as protein leaking directly from decidual cells. If the sample contains amniotic fluid, the test based on the invention cannot be used to show elevation of the IGFBP-1 level due to leaking decidual cells, since the concentration of IGFBP-1 due to the presence of amniotic fluid is higher. Rupture of the foetal membranes can be detected by examination, by quantitative determination of IGFBP-1 or by diagnostic methods such as the one mentioned above (Patent Application PCT/FI91/00413).

Table 1 shows that in pregnant women, the serum concentration of IGFBP-1 can be as high as 600 µg/l. It is therefore evident that a secretion sample contaminated by blood is not well suited for the test according to the invention for predicting the time of delivery. However, this does not represent a diagnostic problem because even a slight bleeding from the cervical canal is considered a risk factor associated with preterm labour. If the bleeding should stop, cervical maturation can be monitored by determining the concentration of IGFBP-1 as described in the present invention.

Examples of situations where the concentration of IGFBP-1 in the vaginal secretion has been monitored during pregnancy are shown in Table 2. Table 3 shows individual cases representing concentrations of IGFBP-1 in extracted cervical secretion in various situations. The IGFBP-1 concentrations shown in said tables were obtained using secretion samples extracted in 0.5 ml of buffer and the quantitative test IGFBP-1 IEMA Test Cat 10831 (Oy Medix Biochemica Ab, Finland).

TABLE 2

| Patient | Gestation weeks + days | IGFBP-1 µg/l | Contractions | Remarks |
|---|---|---|---|---|
| 1 | 30 + 1 | 0 | + | delivery week 41 + 3 |
|   | 32 + 2 | 0 | (+) |   |
|   | 35 + 1 | 0 | + |   |
|   | 37 + 1 | 0 |   |   |
| 2 | 37 + 1 | 0.6 | – | delivery week 41 + 3 |
|   | 39 + 4 | 0 | – | post-term pregnancy |
|   | 41 + 2 | 0 | – | membranes punctured |
| 3 | 31 + 5 | 0 | + |   |
|   | 33 + 4 | 0 | – |   |
|   | 36 + 4 | 0 | + |   |
|   | 38 + 3 | 0 | (+) |   |
|   | 40 + 2 | 0 |   |   |
| 4 | 24 + 1 | 0.6 | + |   |
|   | 25 + 1 | 1.8 | (+) |   |
|   | 27 + 2 | 0 | (+) |   |
|   | 29 + 2 | 0 | (+) |   |
|   | 32 + 2 | 0 | – |   |
| 5 | 28 + 5 | 0 | + | delivery week 38 + 4 |
|   | 30 + 4 | 0 | (+) | emergency section |
|   | 32 + 4 | 0 | – | foetus transverse |
|   | 34 + 4 | 2.3 | (+) | twin pregnancy |
|   | 36 + 3 | 0 | – |   |
| 6 | 32 + 3 | 0 | – | delivery week 40 + 2 |
|   | 36 | 0 | (+) |   |
|   | 39 + 3 | 3.9 | (+) |   |
| 7 | 25 + 3 | 0 | + | delivery week 35 + 2 |
|   | 27 + 5 | 0 | (+) | emergency section |
|   | 29 + 4 | 0 | (+) | twin pregnancy |
|   | 31 + 5 | 0 | (+) |   |
|   | 33 + 6 | 8.8 | (+) |   |
| 8 | 32 + 2 | 0 | – | delivery week 42 + 2 |
|   | 36 + 2 | 0 | – |   |
|   | 40 + 2 | 0 | – |   |
|   | 41 + 6 | 2.5 | – |   |
| 9 | 24 | 3.0 | + | delivery week 33 |
|   | 26 | 0 | (+) | section |
|   | 28 | 0 | (+) | triple pregnancy |
|   | 30 | 0 | – |   |
|   | 31 + 1 | 1.8 | + |   |
| 10 | 29 + 6 | 0.6 | (+) | delivery week 33 + 6 |
|   | 30 + 5 | 0 | – | section |
|   | 31 + 5 | 5.3 | – | triple pregnancy |

TABLE 3

| Patient | Gestation weeks + days | IGFBP-1 µg/l | Contractions | Membranes | Delivery |
|---|---|---|---|---|---|
| A | 41 + 3 | 0 |   | intact | induction |
| B | 35 | 8100 | – | ruptured | 35 + 1 spont. |
| C | 41 + 2 | 0.7 | – | intact | 41 + 6 spont. |
| D | 41 + 5 | 6160 | – | ruptured | 41 + 6 spont. |
| E | 39 | 61 |   | intact | 39 + 1 spont. |
| F | 39 + 2 | 0 | – | intact | induction |
| G | 35 | 1 | (+) | intact | 35 + 6 twins |
| H | 35 | 13 | – | intact | 35 + 6 |
| I | 31 + 5 | 0.4 | – | intact | 40 |

(spont. = spontaneous)

From the data shown in Tables 2 and 3, it can be concluded that the IGFBP-1 level in an extracted secretion sample is normally below the limits of detection of the method, i.e. below about 0.5 µg/l. This can therefore be considered the baseline level. Concentrations above the baseline level indicate the presence of some active process. This, together with clinical information, is used to decide whether any treatment is necessary.

Table 3 shows that, as spontaneous delivery approached in women whose membranes were still intact, the concentration of IGFBP-1 in the extracted sample varied between about 1 and 61 µg/l. Higher concentrations (8100, 6160µ/l) associated with ruptured foetal membranes are clearly distinguishable.

In practice it is difficult to set a definite lowest limit for a clinically significant IGFBP-1 concentration, because many factors affect sampling. This is why the lowest limit of the test should be set to a value just above the baseline level, e.g. 1 µg/l, as the aim is to detect rising values.

A small amount of secretion (100-200 µl) is sufficient for the test. The sample can be taken during a speculum examination, e.g., into a syringe or with a sterile sampling device made for this purpose. In practice, the simplest method is to absorb the secretion into a swab and then extract it into a buffer solution.

Since it is difficult to obtain a specific amount of vaginal or cervical secretion, the samples mentioned in this patent application were extracted into 0.5 ml of buffer, and the IGFBP-1 concentrations mentioned in the description and in the appended claims refer to results obtained from this solution. The IGFBP-1 concentration of the native sample is therefore about five times the concentrations given.

Despite the inaccuracy of sampling, a reliable diagnosis can be obtained since the elevation of the IGFBP-1 concentration is so clear that variations in sampling do not greatly affect interpretation of the results.

The concentration of IGFBP-1 is best determined using an immunological assay, which may be quantitative, semiquantitative or qualitative. In the preferred qualitative embodiment, the measurement range is such that even a slightly elevated concentration of IGFBP-1 is clearly differentiated as positive from the low normal baseline level that is the negative result. In such a case, a first positive signal is obtained when the concentration of IGFBP-1 is over about 0.5 µg/l, preferably over 1 µg/l, and a second positive signal is obtained when the concentration of IGFBP-1 is about 100 µg/l or over.

A semiquantitative determination can be made, for instance, using several reagents indicating different IGFBP-1 concentrations, a positive signal occurring when the IGFBP-1 concentration exceeds predetermined cut-off values such as 1 µg/l, 2.5 pg/l, 5 µg/l, 10 µg/l etc.

The preferred IGFBP-1 test according to the present invention has been developed to give a result as rapidly as possible, which is advantageous both medically and economically in establishing the diagnosis intended in the invention. The sample required can be taken during a gynaecological speculum examination. The sample can also be taken using a swab, into a syringe or with a sampling device made for this purpose.

When binding substances specific to IGFBP-1 only are used, false positive reactions caused by a cross-reaction, i.e. binding of the wrong compound, are eliminated.

According to the present invention, the IGFBP-1 test is preferably performed using two specific monoclonal antibodies, e.g, so that one is attached to a small plastic bead and the other one is coupled to a label, for example an enzyme, such as horseradish peroxidase (HRP). The sample, the enzyme-labelled antibody and the antibody-coated bead in a gripper are placed in a test tube. When the mixture is incubated, the IGFBP-1 present in the sample will become attached both to the bead and to the labelled antibody. After incubation, the bead is removed from the tube and washed under running water. The bead is placed in a tube containing the substrate solution of the enzyme used as label. During incubation, a visible color develops if the sample contains a sufficient amount of IGFBP-1. The solution remains colorless if the sample does not contain IGFBP-1, or if its concentration is too low. A quantitative value is obtained for the IGFBP-1 concentration if the absorbance of the solution is determined photometrically.

The IGFBP-1 test according to the present invention can also be performed by attaching the first antibody to the surface of a membrane developed for such test purposes. The sample is placed in contact with the membrane, and the IGFBP-1 in the sample will bind specifically to the immobilized antibody. A corresponding enzyme-coupled antibody is then added, which in turn binds to the IGFBP-1 now present on the membrane. The membrane is washed and bound enzyme is detected by adding to the washed membrane a precipitating substrate of the enzyme, which changes color in the presence of said enzyme. Thus, when the sample is positive, a visible color develops on the membrane. This kind of test, which is based on an antibody-coated membrane, can be provided, for instance, by attaching such a membrane to a plastic vessel especially designed for the purpose. An absorbent material placed under the membrane will rapidly absorb the test solutions through the membrane when the liquids are pipetted onto the membrane. The membrane can also be attached to a plastic strip, which is then transferred from one solution to another.

A color indicating a positive result can also be obtained otherwise than by labelling the antibody with an enzyme, which in turn causes said change in the color of its substrate. Instead of labelling the antibody with an enzyme, a dye can be used to produce a color indicating a positive result. The intensity of the color of the label bound to the immobilized IGFBP-1 in a positive test situation should be strong enough to be visible. Gold or selenium colloids or disperse dyes can be used for this purpose. The advantage of such dyes is that the test is quicker to perform since a separate substrate reaction phase is not needed. Correspondingly, the antibody can be coupled to colored latex particles. When latex or dye particles are used for direct visual detection a rapid immunochromatographic test method can be used for IGFBP-1. Typically, a membrane is used, and a first antibody is attached to a small area of the membrane. A second color-labelled antibody is attached to another area by drying. The second antibody starts to migrate across the membrane when a liquid sample is added. If the sample contains a sufficient amount of IGFBP-1, a colored zone will develop at the point where the antigen bound to the labelled antibody binds also to the antibody immobilized onto the membrane. If the sample is negative, no colored zone develops, and the dye migrates over the membrane.

An IGFBP-1 test can also be performed using the agglutination principle. Here, the visible reaction takes the form of an agglutination of, say, antibody-coated particles such as latex, the antigen in the sample causing bonds to be formed between the particles. Alternatively, detection can be based on the inhibition of agglutination.

In addition to specific antibodies, methods and test kits according to the present invention can make use of other specific IGFBP-1 binding substances as well as combinations of the two. This allows the natural binding characteristics of IGFBP-1 to substances like IGF (Insulin-like Growth Factor) to be exploited.

The test can also be performed using the assay methods set out in FI patent 84863, the contents of which are included herein by reference.

The IGFBP-1 test methods according to the present invention can greatly ease the problems related to assessing the time of delivery. In post-term pregnancies the invention makes it possible to reduce maternal and foetal morbidity by determining the optimal time for induction of labour. This, in turn, will reduce the number of cesarean sections. It will also make it easier to decide on an emergency section as the primary mode of delivery in cases in which the cervix does not show any signs of dilation. Excluding neonatal malformations, preterm labour is the main reason for neonatal morbidity and mortality. The problem can be considerably alleviated by prophylactic treatment if this can be given early enough to the right patients.

The decisions outlined above are significant both economically and medically: economically in terms of the cost of hospitalization, and medically in terms of greater maternal and foetal well-being and lower mortality.

The test kit according to the present invention contains a reagent based on a specific binding substance for IGFBP-1. Depending on the test method employed, the reagent may be a binding substance solution, a solid phase like a bead or membrane coated with a specific binding substance, or latex or dye particles. For example, in a one-step assay, the kit may also contain a combination of the above mentioned components. The specific binding substance should preferably be a monoclonal antibody specific to IGFBP-1.

In addition to the reagent mentioned above, the kit preferably contains a label that is able to detect a sufficient concentration of IGFBP-1 in the sample after the binding reaction. The label detecting the binding reaction should preferably be a signal-producing label coupled to another antibody to IGFBP-1. The label which is coupled to another antibody to IGFBP-1 may be an enzyme, a radioactive isotope or a compound that can be recognized by its color. If the label is an enzyme, the test kit preferably also contains a suitable substrate.

In addition to the essential reagents, the test kit preferably also contains a solution for handling the sample (e.g. for extracting the sample from the swab). A suitable solution would be an extraction buffer, e.g., a phosphate buffer containing a protective protein and having a pH close to the physiological pH.

The test kit may also contain a sampling instrument, such as a sterile swab, a disposable syringe or a device specially developed for the test. If the result is to be quantified, the kit may also contain the relevant standards.

The test kit may also comprise a simple device for taking a vaginal secretion sample and a suitable buffer solution for performing the test. The test kit may also comprise an antibody-coated test strip that the patient herself can insert into the vagina.

The preferred test kit according to the present invention is a combination kit, allowing two tests to be performed simultaneously on one sample. One test will assess the maturity of the cervix, while the other one will detect rupture of the foetal membranes, e.g., as described in Patent Application PCT/FI91/00413. Such a combination kit could be based on the immunochromatographic principle in which case it will comprise a membrane to which are attached two zones of an IGFBP-1 binding substance. Said zones are of different strength. One zone is used to indicate a low concentration of IGFBP-1 in the sample, which in turn indicates maturity of the cervix. If the concentration is high enough to indicate the presence of amniotic fluid, a color reaction will develop in both zones. Different dilutions of the label can also be used, or different colored labels may be used, positive test results being indicated by zones of different colors.

The test may also comprise several zones that give a positive signal when the concentration of IGFBP-1 exceeds cut-off values such as 1 µg/l, 5 µg/l, 10 µg/l and 100 µg/l.

The Examples below illustrate how the test according to the invention can be carried out without, however, limiting it in any way.

EXAMPLE 1

A sample was taken from the vagina of a pregnant woman (gestation week 39+3) using a Dacron swab. The swab was held in the vagina for about 15 seconds to allow a sufficient amount of secretion to be absorbed into said swab. The sample was extracted into 0.5 ml of an assay buffer (buffer solution containing a stabilizer and a surfactant). The extracted sample was centrifuged and the concentration of IGFBP-1 was determined quantitatively from the supernatant (IGFBP-1 IEMA TEST Cat 10831-ETMB, manufactured by Oy Medix Biochemica Ab, Finland).

The concentration of IGFBP-1 in the supernatant was 3.9 µg/l, indicating that the cervix was mature. The patient gave birth six days later.

EXAMPLE 2

Plastic beads are coated with IGFBP-1 antibody (6305, Medix Biochemica). Another IGFBP-1 antibody (6303, Medix Biochemica) is coupled with an enzyme label (horseradish peroxidase, HRP). Phosphate buffer (pH 7.4) containing 0.3% bovine serum albumin (BSA) is used as assay buffer. The buffer also contains a detergent and preservatives. A rapid IGFBP-1 test is performed according to the following instructions.

Performing the rapid IGFBP-1 test:

1. 200 µl of 6303-HRP label (diluted 1:50 in assay buffer) are pipetted into a sample tube.

2. 100 µl of sample (extracted into 0.5 ml of buffer) are added to the tube.

3. An IGFBP-1 antibody-coated bead in a gripper is placed into the tube. It is incubated for 5 minutes.

4. The bead and the gripper are removed from the solution and the bead is washed under running water for 30 seconds.

5. The washed bead including the gripper are transferred to 400 41 of substrate solution (2,2'-azino-di-(3-ethyl-benzthiazoline sulfonate(6)], ARTS) in a clear tube.

6. The tube is allowed to stand in a dark protected bottle for 5 minutes.

7. The color of the solution is either inspected immediately or the reaction is stopped by adding an inhibitor solution (200 µl) and then inspecting the solution: a colorless solution indicates a negative result and green a positive result.

EXAMPLE 3

A narrow zone of a nitrocellulose membrane strip is coated with an IGFBP-1 antibody (6305, Medix Biochemica). Coloured latex particles are coated with another IGFBP-1 antibody (6303, Medix Biochemica). The coated latex particles are dried onto one end of the membrane strip containing the antibody zone. A rapid IGFBP-1 test is performed on the membrane according to the following instructions.

Performing the IGFBP-1 membrane test

1. A few drops of the sample are pipetted onto that part of the strip holding the dried latex particles.

2. Incubation for a few minutes allows the sample to migrate across the membrane. The latex particles, together with the liquid, will move over the antibody-coated zone to the other end of the strip.

3. The strip is inspected. The presence of a colored zone indicates a positive result.

EXAMPLE 4

A small area of a nylon membrane is coated with IGFBP-1 antibody (6305, Medix Biochemica). The coated membrane is placed on a plastic cup-like vessel so that immediately beneath and in contact with the membrane is an absorbent material (treated cellulose). Another IGFBP-1 antibody (6303, Medix Biochemica) is coupled to an enzyme label (horseradish peroxidase, HRP). A rapid IGFBP-1 test is performed according to the following instructions.

1. A few drops of the sample solution are pipetted onto the membrane and the solution is allowed to absorb through the membrane.

2. As much wash solution as the cup will hold (about 1 ml) is pipetted onto the membrane and the solution is allowed to absorb through the membrane.

3. A few drops of the label solution are pipetted onto the membrane and the solution is allowed to absorb through the membrane.

4. About 1 ml of a wash solution is pipetted onto the membrane and the solution is allowed to absorb through the membrane.

5. A few drops of precipitating substrate of the enzyme are pipetted onto the membrane and the solution is allowed to absorb through the membrane.

6. The membrane is inspected. A colored zone indicates a positive result.

The immunometric methods described above illustrate how the test according to the present invention may be carried out. It will be evident to the person skilled in the art that the methods may be varied and modified within the above specification and the appended claims without deviating from the scope of the invention.

The invention claimed is:

1. A method for identifying a patient with intact foetal membranes possessing risk factors indicative of preterm delivery comprising:
   a) detecting a first level of IGFBP-1 at a first time interval in an essentially blood-free vaginal or cervical secretion sample from said patient with an antibody that recognizes IGFBP-1;
   b) detecting a test level of IGFBP-1 at a second time interval in an essentially blood-free vaginal or cervical secretion sample from said patient with an antibody that recognizes IGFBP-1;
   c) comparing said levels of IGFBP-1 to a high level of 100 µg/l and a low level of less than 1.0 µg/l;
   d) comparing said test level of IGFBP-1 to said first level;
   e) identifying a test level of IGFBP-1 that is less than 100 µg/l and equal to or greater than 1 µg/l; and f) providing medical advice designed to prevent preterm delivery to said patient where said sample has an IGFBP-1 level that is less than 100 μg/l and equal to or greater than 1 μg/l but which is higher than said first level, wherein said test level of IGFBP-1 being less than 100 μg/l and equal to or greater than 1 μg/l but which is higher than said first level, despite intact foetal membranes, indicates that said patient possesses risk factors indicative of preterm delivery.

2. The method according to claim 1, wherein said level of IGFBP-1 is determined by a quantitative, semiquantitative or qualitative immunological assay.

3. The method according to claim 1, wherein said secretion sample is obtained from the cervix.

4. A method for assessing the maturity of a cervix and predicting a time of delivery in patients with intact foetal membranes and a post-term pregnancy comprising:
   a) detecting a first level of IGFBP-1 at a first time interval in an essentially blood-free vaginal or cervical secretion sample from said patient with an antibody that recognizes IGFBP-1;
   b) detecting a test level of IGFBP-1 at a second time interval in an essentially blood-free vaginal or cervical secretion sample from said patient with an antibody that recognizes IGFBP-1
   c) comparing said levels of IGFBP-1 to a high level of 100 μg/l and a low level of less than 1.0 μg/l;
   d) comparing said test level of IGFBP-1 to said first level;
   e) identifying a test level of IGFBP-1 that is less than 100 μg/l and equal to or greater than 1 μg/l; and
   f) providing medical advice designed to promote a safe delivery by said patient where said sample has an IGFBP-1 level that is less than 100 μg/l and equal to or greater than 1 μg/l but which is higher than said first level, wherein said test level of less than 100 μg/l and equal to or greater than 1 μg/l but which is higher than said first level, despite intact foetal membranes, indicates maturation of the cervix of said patient and impending delivery.

5. The method according to claim 4, wherein said level of IGFBP-1 is determined by a quantitative, semiquantitative or qualitative immunological assay.

6. The method according to claim 4, wherein said secretion sample is obtained from the cervix.

7. A method for assessing a time for induction of labor in post-term pregnancy patients with intact foetal membranes comprising:
   a) detecting a first level of IGFBP-1 at a first time interval in an essentially blood-free vaginal or cervical secretion sample from said patient with an antibody that recognizes IGFBP-1;
   b) detecting a test level of IGFBP-1 at a second time interval in an essentially blood-free vaginal or cervical secretion sample from said patient with an antibody that recognizes IGFBP-1;
   c) comparing said levels of IGFBP-1 to a high level of 100 μg/l and a low level of less than 1.0 μg/l;
   d) comparing said test level of IGFBP-1 to said first level;
   e) identifying a test level of IGFBP-1 that is less than 100 μg/l and equal to or greater than 1 μg/l, and
   f) initiating induction of labor for said patient where said sample has an IGFBP-1 level that is less than 100 μg/l and equal to or greater than 1 μg/l but which is higher than said first level, wherein said test level of less than 100 μg/l and equal to or greater than 1 μg/l but which is higher than said first level, despite intact foetal membranes, indicates maturation of the cervix of said patient and impending delivery.

8. The method according to claim 7, wherein said level of IGFBP-1 is determined by a quantitative, semiquantitative or qualitative immunological assay.

9. The method according to claim 7, wherein said secretion sample is obtained from the cervix.

* * * * *